(12) United States Patent
Hoggarth et al.

(10) Patent No.: US 10,561,533 B2
(45) Date of Patent: *Feb. 18, 2020

(54) COMPOSITION FOR A WOUND DRESSING

(71) Applicant: MEDTRADE PRODUCTS LIMITED, Crewe, Cheshire (GB)

(72) Inventors: Andrew Hoggarth, Crewe (GB); Craig Hardy, Cardigan (GB)

(73) Assignee: MEDTRADE PRODUCTS LIMITED, Crewe (GB)

(*) Notice: Subject to any disclaimer, the term of this patent is extended or adjusted under 35 U.S.C. 154(b) by 0 days.

This patent is subject to a terminal disclaimer.

(21) Appl. No.: 15/546,644

(22) PCT Filed: Jan. 27, 2016

(86) PCT No.: PCT/GB2016/050179
§ 371 (c)(1),
(2) Date: Jul. 26, 2017

(87) PCT Pub. No.: WO2016/120621
PCT Pub. Date: Aug. 4, 2016

(65) Prior Publication Data
US 2018/0014975 A1   Jan. 18, 2018

(30) Foreign Application Priority Data

Jan. 27, 2015 (GB) .................................. 1501333.7

(51) Int. Cl.
*A61F 13/00* (2006.01)
*A61L 15/46* (2006.01)
*A61L 15/20* (2006.01)

(52) U.S. Cl.
CPC .. *A61F 13/00008* (2013.01); *A61F 13/00029* (2013.01); *A61L 15/20* (2013.01);
(Continued)

(58) Field of Classification Search
CPC .... A61L 15/28; A61L 2300/404; A61L 15/46; A61L 15/20; A61F 13/00008; A61F 2013/00931; A61F 13/00029
See application file for complete search history.

(56) References Cited

U.S. PATENT DOCUMENTS

2014/0275291 A1* 9/2014 McGrath ................... C08L 5/08
514/777

FOREIGN PATENT DOCUMENTS

CN     101081308 A     12/2007
CN     101239199 A     8/2008
(Continued)

OTHER PUBLICATIONS

Intellectual Property Office; Search Report under Section 17 for Patent Application No. GB1501333.7 dated Jul. 20, 2015; 1 page.
(Continued)

*Primary Examiner* — Jianfeng Song
(74) *Attorney, Agent, or Firm* — Schwabe, Williamson & Wyatt, P.C.

(57) ABSTRACT

The present invention relates to a composition that can be used as or as part of a wound dressing and to wound dressings comprising the same. More specifically, the present invention relates to a composition that disrupts and kills bacteria within a biofilm and also prevents biofilm formation. The composition comprises a first component selected from the group consisting of chitosan, chitin, derivatives of chitosan, derivatives of chitin, and combinations thereof; at least one triprotic acid and at least one solubilising acid.

14 Claims, 8 Drawing Sheets

(52) U.S. Cl.
CPC ..... *A61L 15/46* (2013.01); *A61F 2013/00931* (2013.01); *A61L 2300/404* (2013.01)

(56) References Cited

FOREIGN PATENT DOCUMENTS

| | | | | |
|---|---|---|---|---|
| KR | 1329261 | * | 11/2013 | ........... D04H 1/4328 |
| WO | 2012091636 A2 | | 7/2012 | |
| WO | 2014072721 A1 | | 5/2014 | |

OTHER PUBLICATIONS

International Search Report for Patent Application No. PCT/GB2016/050179 dated May 10, 2016; 5 pages.

Ross P. Carlson et al: "Anti-biofilm properties of chitosan-coated surfaces", Journal of Biomaterials Science. Polymer Edition., vol. 19, No. 8, Jan. 1, 2008 (Jan. 1, 2008), NL, pp. 1035-1046, XP055269153, ISSN: 0920-5063, DOI: 10.1163/156856208784909372; 12 pages.

Anonymous; "Mechanical robustness of Pseudomonas aeruginosa biofilms," Jul. 12, 2011; 9 pages.

\* cited by examiner

COMPOSITION FOR A WOUND DRESSING

CROSS REFERENCE TO RELATED APPLICATIONS

The present application is a national phase entry under 35 U.S.C. § 371 of International Application No. PCT/GB2016/050179, filed Jan. 27, 2016, entitled "COMPOSITION FOR A WOUND DRESSING", which claims priority to GB Application No. 1501333.7 filed on Jan. 27, 2015, which are hereby incorporated by reference in their entireties.

The present invention relates to a composition that can be used as or as part of a wound dressing and to wound dressings comprising the same. More specifically, the present invention relates to a composition that disrupts and kills bacteria within a biofilm and also prevents biofilm formation.

A useful explanation of biofilms is provided by Philips P L, et al., *Biofilms Made Easy, Wounds International* 2010, 1(3) and is summarised herein. A biofilm is any group of microorganisms in which cells effectively stick to each other on a surface. A biofilm can typically be a complex microbial community containing bacteria and fungi. The microorganisms are frequently embedded within a self-produced matrix of extracellular polymeric substance (EPS). Biofilm EPS, which is also referred to as slime (although it will be appreciated that not everything referred to as slime is a biofilm), is a polymeric conglomeration generally composed of extracellular DNA, proteins, and polysaccharides. The matrix of EPS can attach the biofilm firmly to living or non-living surfaces.

It is known that biofilms form on the surfaces of medical devices, such as urinary catheters, implants, and sutures. They are problematic since they are a contributor to diseases that are characterised by an underlying bacterial infection and chronic inflammation.

The field of the present invention is principally wound care. Biofilms are commonly found in wounds but it is only relatively recently that they have been accepted as causing a delay in wound healing. It has even been suggested that almost all chronic wounds have biofilm communities on at least a part of the wound bed.

Biofilms may form on living or non-living surfaces and can be prevalent in natural, industrial and hospital environments. Under natural conditions, microorganisms such as bacteria may attach to surfaces and form biofilms. As the bacteria multiply, they become more firmly attached to the surface. Once attached, the bacteria secrete EPS to form a protective matrix. This then leads to small bacteria colonies forming an initial biofilm. Over time, the biofilm can disperse and attach to other parts of the wound bed, forming new biofilm colonies.

The formation of biofilms can occur relatively quickly, with a biofilm capable of forming in less than 24 hours.

It is thought that biofilms stimulate a chronic inflammatory response in an attempt to rid the wound of the biofilm. This response results in abundant neutrophils and macrophages surrounding biofilms. These inflammatory cells secrete high levels of reactive oxygen species (ROS) and proteases (matrix metalloproteinases (MMPs) and elastase). The proteases can help to break down the attachments between biofilms and the tissue, dislodging the biofilms from the wound. However, the ROS and proteases also damage normal and healing tissues, proteins and immune cells. The chronic inflammatory response is not always successful in removing the biofilm and it has been hypothesised that the response is in the interest of the biofilm. By inducing an ineffective inflammatory response, the biofilm protects the microorganisms it contains and increases exudate production, which provides a source of nutrition and helps to perpetuate the biofilm.

At present, one of the most effective methods for reducing the adverse effects of biofilms is to physically remove the biofilm, known as debridement. Debridement involves the removal of dead and contaminated tissue from the wound. However, such a process has its limitations, since no form of debridement can remove all of a biofilm. Consequently, the biofilm has the potential to reform within a short period of time. As a result of this, a patient has to undergo debridement on a frequent basis.

Attempts to prevent a biofilm reforming have also been researched. Predominantly, these methods use antimicrobial agents to kill microorganisms. However, there are several limitations to this method in the sense that the antimicrobial agents can be used in different ways and patient sensitivities and allergies need to be considered.

There is therefore a need to develop improved methods of killing bacteria within a biofilm and also preventing the biofilm from reforming.

The present invention has been made from a consideration of the aforementioned limitations and problems.

According to a first aspect of the present invention, there is provided a composition comprising a first component selected from the group consisting of chitosan, chitin, derivatives of chitosan, derivatives of chitin, and any combination thereof; at least one triprotic acid and at least one solubilising acid.

It has been surprisingly discovered that a composition comprising the first component, at least one triprotic acid and at least one solubilising acid is capable of disrupting and preventing biofilm formation and has an antimicrobial effect on microorganisms within the biofilm.

The biofilm referred to herein is preferably a microbial based biofilm, although the invention is not limited to such.

The term 'triprotic acid' (which may also be referred to herein as a 'tribasic acid') is used herein to refer to an acid that has three hydrogen ions to donate to a base in an acid-base reaction. In other words, a triprotic molecule has three replaceable hydrogen atoms.

The composition may comprise one or more triprotic acids. The composition may therefore comprise two, three, four or more triprotic acids. Typically, the composition comprises one triprotic acid.

The triprotic acid may be selected from the group consisting of citric acid, phosphoric acid, or mixtures thereof. Preferably, the triprotic acid is citric acid.

Triprotic acids may be in the form of granules, flakes, powders or solutions. Typically, the triprotic acid is sourced in the form of a powder.

In preparing the composition of the present invention, the triprotic acid is typically in the form of an acid solution. Such a solution is prepared by dissolving a quantity of triprotic acid, typically in powder form, in a volume of water and/or a solvent. The solvent may be aqueous or non-aqueous, but is preferably non-aqueous.

The composition may comprise a mixture of the first component and the triprotic acid. The triprotic acid may be contacted with the first component.

Typically, the triprotic acid is absorbed into, or coated onto, at least a portion of the first component. Preferably, the triprotic acid is coated onto at least a portion of the surface of the first component. More preferably, the triprotic acid is coated onto substantially all of the surface of the first component.

Antimicrobial agents are generally referred to as substances that kill, or inhibit the growth of, microorganisms. It is generally accepted in wound healing that for a substance to claim antimicrobial efficacy it must demonstrate a Log 4 bacterial kill rate.

The term 'antimicrobial' is used herein to refer to an agent or substance capable of demonstrating a Log 4 bacterial kill rate within 24 hours. Conversely, the term 'non-antimicrobial' is used herein to refer to an agent or substance that demonstrates less than a Log 4 bacterial kill rate within 24 hours.

The first component may be non-antimicrobial.

The ratio of the first component to the at least one triprotic acid may be at least 2:1.

The ratio of the at least one triprotic acid to the at least one solubilising acid is at least 1:1.

The first component may be in the form of fibres, granules, flakes, powder, or combinations thereof.

The first component may be fully or partially coated with the triprotic acid.

Typically, the first component comprises fibres. The fibres may be woven or nonwoven. Preferably, the fibres are nonwoven. The fibres may be fully or partially coated with the triprotic acid.

Alternatively, the composition may comprise separate portions of the first component and triprotic acid. For example, the first component may be in the form of fibres, granules, flakes, powder, one or more sheets or combinations thereof and the triprotic acid may be in the form of granules, flakes, or a powder whereby the first component and the triprotic acid are located in separate portions of the composition. The separate portions may for example be in the form of layers. Alternatively, the triprotic acid and the first component may be mixed.

Additionally or alternatively, the triprotic acid may be associated with a carrier material. The composition may therefore comprise a first component selected from the group consisting of chitosan, chitin, derivatives of chitosan, derivatives of chitin, and combinations thereof; and at least one triprotic acid, wherein the triprotic acid is associated with a carrier material.

The triprotic acid may be absorbed into, or coated onto, the carrier material. The carrier material can act as a carrier for the triprotic acid. In such embodiments, the triprotic acid should not react or irreversibly bond with the carrier material. The carrier material may comprise any suitable material that can absorb, receive or act as a carrier for a triprotic acid. Typical materials include, but are not limited to, polymers such as cellulose, cellulose derivatives (e.g. ethyl cellulose, methyl cellulose, etc.), cotton, alginate, viscose, polypropylene, polyethylene or any combination of such materials. Preferably, the carrier material is viscose.

Typically, the carrier material is fibrous. In some embodiments, the first component and the carrier material may be combined together to make a non-woven fabric. The first component and the carrier material may be carded or needled together.

Preferably, however, the composition does not comprise a carrier material. The triprotic acid is preferably coated onto at least a portion of the first component as explained hereinbefore.

The triprotic acid may be coated onto the first component and/or the carrier material by any suitable means known in the art.

Generally, a triprotic acid, typically in powder form, is dissolved in water to form an acid solution. The acid solution may then be mixed with a solvent. The first component is then mixed with the acid solution/solvent mixture. The solvent and optionally at least a portion of the water may be removed by evaporation, for example, to provide a solid composition of the present invention. Typically, the composition comprises the triprotic acid coated onto the first component.

Alternatively, the triprotic acid may be mixed with water and/or a solvent as explained above and sprayed onto the first component.

Preferably, the first component is not dissolved in a solvent during preparation of the composition. Preferably, the first component is insoluble in the acid solution or acid solution/solvent mixture.

It has been observed that preparing an initial composition of the first component and the triprotic acid without initially dissolving the first component in a solvent, and/or whereby the first component does not dissolve in the acid solution/solvent mixture, enables the efficient preparation of a composition having a greater quantity of the first component that can be delivered to the wound. This is beneficial over utilising a first component that is initially dissolved in a solvent, as the overall quantity of first component available is diluted by the presence of the solvent. Moreover, in situations where a first component is dissolved during preparation, the final composition cannot be in the form of fibres, granules or powder, which limits the potential uses and forms of the composition. The first component may therefore be insoluble in water and solvent.

In cases where the first component comprises chitosan fibres, the solvent is preferably a non-aqueous solvent such as isopropyl alcohol.

The triprotic acid is preferably delivered in the form of an acid solution. The acid solution (acid in water) may have a concentration of from around 5-80%, preferably from around 20-60% and most preferably from around 40-50%.

The triprotic acid may be present in the composition in an amount greater than around 2% of the first component, preferably greater than around 5% of the first component, more preferably greater than around 10% of the first component and most preferably greater than around 25% of the first component. The triprotic acid may be present in the composition in an amount of at least around 2% of the first component, preferably at least around 5% of the first component, more preferably at least around 10% of the first component and most preferably at least around 25% of the first component.

The triprotic acid may be present in an amount of around 2-75% of the first component, preferably around 10-75% of the first component, more preferably around 20-75% of the first component and most preferably in an amount of around 25-60% of the first component. Good results have been observed with triprotic acid present in an amount of around 60% of the first component. The percentage values of acid referred to represent relative amounts of triprotic acid compared to the total amount of the first component in the composition. For example, if the total amount of the first component in the composition was 1 g, a composition comprising 20% triprotic acid would contain 0.2 g of the triprotic acid.

The first component is selected from the group consisting of chitosan, chitin, derivatives of chitosan, derivatives of chitin, and any combination thereof.

The term 'derivative' is used herein to refer to a compound that is derived from chitosan or chitin following one or more chemical reactions or modifications. The one or more chemical reactions or modifications may involve substitution of one or more of the amino or hydroxyl protons in chitosan or chitin; or partial deacetylation of chitin. For example, a chitin derivative may include a partially deacetylated chitin, which may have different percentages of deacetylation, as desired. Typically, the partially deacetylated chitin suitable for use in the present invention has a deacetylation degree of at least about 50%, more typically at least about 75% and most typically at least about 85%. Also included within the terms 'chitosan or chitin derivatives' are reaction products of chitosan or chitin with other compounds. Such reaction products include, but are not limited to, carboxymethyl chitosan, hydroxyl butyl chitin, N-acyl chitosan, O-acyl chitosan, N-alkyl chitosan, O-alkyl chitosan, N-alkylidene chitosan, N-arylidene chitosan, O-sulfonyl chitosan, sulphated chitosan or chitin, phosphorylated chitosan or chitin, nitrated chitosan or chitin, deoxyhalo chitosan, alkalichitin, alkalichitosan, or metal chelates with chitosan, organic salts, etc. Chitosan or chitin derivatives, including those referred to herein, may also contain functional groups linked to them via covalent or non-covalent bonds.

Typically, the first component is chitosan or a chitosan derivative. Preferably, the first component is chitosan.

Chitosan is a derivative of solid waste from shellfish processing and can be extracted from fungus culture. It is a cationic polymeric material that is insoluble in water. Chitosan is a known haemostat for use in wound dressings. The term 'haemostat' is used herein to refer to any agent which is capable of producing a clot or plug which stops or reduces bleeding when it comes into contact with blood or other bodily fluid, such as wound exudate, from a physiological target site or wound site of a human or animal.

There are many different types of chitosan that may be used as a material in wound dressings, with different absorption properties. The different types of chitosan may have different molecular weights, different degrees of deacetylation, different arrangements of β-(1-4)-linked D-glucosamine and N-acetyl-D-glucosamine monomers, different chiral forms or they may be derived from different species or sources (and fungi), or may have been treated differently during manufacture. Each and all of these different variations of chitosan materials are envisaged for use within the present invention.

The chitosan first component may have a degree of deacetylation of greater than 70%, preferably greater than 80% and more preferably greater than 85%.

Chitosan materials can exhibit gelling properties when in the form of a salt. To obtain a chitosan salt, chitosan is typically mixed with an appropriate acid. The gelling properties of chitosan salts make them desirable for use as materials in wound dressings.

The chitosan and/or chitosan derivative may be in any suitable form, such as for example, fibres, granules, powder, flakes, sheet, foam, freeze dried foam, compressed foam, film, perforated film, beads, and combinations of two or more of the aforesaid. Typically, the chitosan and/or chitosan derivative is in the form of fibres. Preferably, the fibres are nonwoven. The fibres can be of any desired diameter or length and can be formed into a textile fabric or a pad for use.

Typically, the molecular weight of the first component used in the composition of the present invention is less than about 2,000,000, more typically less than about 1,000,000, and even more typically less than about 500,000, and most typically less than about 175,000.

The first component in a 1% acetic acid solution may have a viscosity of greater than 150 cps.

The composition of the present invention comprises a solubilising acid.

The term 'solubilising acid' is used herein to refer to an acid which, when applied to or associated with the first component, makes the first component more soluble in aqueous bodily fluids.

The composition may comprise one or more solubilising acids. The composition may therefore comprise two, three, four or more solubilising acids. Typically, the composition comprises one solubilising acid.

The solubilising acid may be selected from the group consisting of succinic acid, malic acid, sulphuric acid, acrylic acid, lactic acid, formic acid, acetic acid, hydrochloric acid, nitric acid, and mixtures of any one or more thereof.

The solubilising acid may preferably be a monoprotic acid.

The term 'monoprotic acid' (which may also be referred to herein as a 'monobasic acid') is used herein to refer to an acid that has one hydrogen ion to donate to a base in an acid-base reaction. In other words, a monoprotic molecule has one replaceable hydrogen atom.

The monoprotic acid may be selected from the group consisting of lactic acid, formic acid, acetic acid, hydrochloric acid, nitric acid, and mixtures of any one or more thereof.

Preferably, the monoprotic acid is lactic acid, acetic acid or a mixture thereof. Most preferably, the monoprotic acid is lactic acid.

The solubilising acid may be in the form of granules, flakes, powder or solution. Typically, the solubilising acid is in the form of a solution. Such a solution is prepared by dissolving a quantity of solubilising acid in a volume of water and/or solvent.

The composition comprises a mixture of the first component, at least one triprotic acid and at least one solubilising acid.

The solubilising acid may be mixed with the triprotic acid and contacted with the first component in the same manner as described above in relation to the triprotic acid alone. Alternatively, the triprotic and solubilising acids may be contacted with separate portions of the first component and then brought together in the composition. For example, where the first component is in the form of fibres, a selection of the fibres may be partially or fully coated with triprotic acid and a separate selection of the fibres may be partially or fully coated with a solubilising acid.

Typically, the solubilising acid will be mixed with the triprotic acid and contacted with the first component.

The at least one solubilising acid or the mixture of at least one solubilising acid and at least one triprotic acid may be absorbed into, or coated onto, at least a portion of the first component. Preferably, the at least one solubilising acid or the mixture of at least one solubilising acid and at least one triprotic acid is coated onto substantially all of the surface of the first component. In some embodiments, the triprotic acid may be absorbed into, or coated onto, at least a portion of the first component and the solubilising acid can then be absorbed into, or coated onto, at least a portion of this, or vice versa.

Alternatively, the composition may comprise separate portions of the first component, the at least one triprotic acid and the at least one solubilising acid. For example, the first component may be in the form of fibres, granules, flakes, powder, sheet or combinations thereof and the triprotic and solubilising acids may be in the form of granules, flakes and/or a powder, whereby the first component and the acids are located in separate portions of the composition. For example, the separate portions may for example be in the form of layers. Alternatively, the first component, triprotic acid and solubilising acid may be mixed.

In some embodiments, the at least one triprotic acid and the at least one solubilising acid may be associated with the same or separate carrier materials. The composition may therefore comprise a first component selected from the group consisting of chitosan, chitin, derivatives of chitosan, derivatives of chitin, and combinations thereof; at least one triprotic acid and at least one solubilising acid, wherein the triprotic acid and/or the solubilising acid are associated with the same or separate carrier materials.

The solubilising acid may be associated with the carrier material in the same way as described herein with reference to the triprotic acid.

The solubilising acid may be coated onto the first component and the triprotic acid may be coated onto a carrier material, or vice versa.

The first component may comprise fibres coated with solubilising acid and the carrier material may be coated with triprotic acid. The carrier material may be viscose.

The at least one solubilising acid may be coated onto the first component and/or the carrier material by the same means as described for the triprotic acid.

The first component may be partially or completely coated with solubilising acid.

The solubilising acid is preferably delivered in the form of an acid solution. The acid solution (acid in water) may have a concentration of at least around 40%, preferably at least around 60% and most preferably at least around 80%.

The at least one solubilising acid may be present in an amount greater than around 2% of the first component, preferably greater than 5% of the first component, and more preferably greater than around 10% of the first component. The at least one solubilising acid may be present in the composition in an amount of at least around 2% of the first component, preferably at least around 5% of the first component, more preferably at least around 10% of the first component and most preferably at least around 25% of the first component.

The at least one solubilising acid may be present in an amount of around 2-50% of the first component, preferably around 10-40% of the first component, or more preferably around 20-30% of the first component. Preferably, the at least one solubilising acid may be present in an amount of around 25% of the first component. In the same way as for the triprotic acid, the percentage values referred to represent relative amounts of solubilising acid compared to the total amount of the first component.

Without the presence of a solubilising acid, it has been observed that a higher amount of triprotic acid in the composition results in a greater efficacy against microorganisms. Such composition may comprise triprotic acid in an amount of at least around 25%, preferably at least around 35%, more preferably at least around 50% and most preferably at least around 60% of the first component.

However, it has been discovered in development that a composition having a solubilising acid content of around 15-30% of the first component can reduce the amount of triprotic acid required to have the desired effect. For example, a composition having a triprotic acid content of greater than 20% has been shown to produce comparable results to a composition having a solubilising acid content of 15-20% but a reduced triprotic acid content of around 5% or less.

Thus, an embodiment of the present invention comprises a composition comprising a first component selected from the group consisting of chitosan, chitin, derivatives of chitosan, derivatives of chitin, and combinations thereof; 20-75% of at least one triprotic acid and 10-40% of at least one solubilising acid.

Good results have been observed for a composition having a solubilising acid content of from 20-35%, particularly 25-30%, of the first component and a triprotic acid content of from 25-45%, particularly 30-40%, of the first component.

The combined acid may be present in the composition in an amount of at least around 4% of the first component, preferably at least around 10% of the first component, more preferably at least around 25% of the first component and most preferably at least around 45% of the first component.

The composition of the present invention may be in the form of granules, flakes, fibres, powder, non-woven textile, or a knitted textile, a gel, a hydrogel sheet, a hydrogel and/or a film. The fibres may be woven or nonwoven. Preferably, the fibres are nonwoven.

Typically, the composition is in the form of fibres. More typically, the composition is in the form of nonwoven fibres or a nonwoven textile.

Alternatively, the composition may be in the form of a gel, hydrogel or liquid. When in these forms the composition may be utilised without further modification (e.g. it may be applied directly to a wound) or the composition may be applied to a delivery mechanism.

A hydrogel is made by obtaining a solution of triprotic and solubilising acid in water, optionally mixing the solution with a solvent and adding the first component to the solution. The first component will absorb the solution and gel. The extent of gelling and strength of the gel can be varied by the amount of first component added to the solution. The greater the amount of first component in the solution the stronger the gel, and vice versa. The gel can then be dried to varying extents depending on the form of the composition desired.

Alternatively, a hydrogel is made by obtaining a composition of the present invention in dry-form, e.g. granules, flakes, fibres, powder, textile, and mixing with water. The composition will absorb water and gel. Again, the extent of gelling and strength of the gel can be varied by the amount of composition mixed with water or the amount of water mixed with the composition. The greater the amount of the composition relative to the water, the stronger the gel, and vice versa. The gel can then be dried to varying extents depending on the form of the composition desired.

For example, a hydrogel sheet may be obtained by transferring the hydrogel into a mould, such as a tray, and drying the hydrogel to an extent so as not to remove all water content but remove sufficient water content to form a gel.

Alternatively, a dry film may be obtained by transferring the hydrogel into a mould, such as a tray, and drying the hydrogel to an extent whereby substantially all water is removed. The resulting composition is in the form of a dry film. The film is preferably flexible.

The delivery mechanism may include a polyurethane foam, a polyurethane film, a woven textile, a superabsorbent material, a medical device such as a catheter, a stent, and the like. The delivery mechanism may comprise more than one of each of the aforesaid components and/or may comprise a combination of one or more of the foregoing.

For example, the delivery mechanism may comprise one or more polyurethane foams and a polyurethane film. Alternatively, the delivery mechanism may comprise a woven viscose textile.

The term 'superabsorbent material' is used herein to refer to a hydrophilic material that is water-swellable, but not water soluble, and which is capable of absorbing fluid to greater than 2000% with a fluid retention of greater than 85%. Preferably, the superabsorbent material is capable of absorbing fluid to greater than 2500% with a fluid retention of greater than 90%.

The term 'water-swellable' is used herein to refer to a material that, when contacted with water or water-containing fluid, will absorb the fluid and swell, but will not substantially dissolve in that fluid.

The term 'water soluble' is used herein to refer to a material that, when contacted with water or a water-containing fluid, will dissolve in that fluid.

The superabsorbent material may be selected from polymeric materials such as poly(vinyl) alcohol (PVA), poly(ethylene oxide) (PEO) and poly(acrylic acid). The superabsorbent material may be chemically modified. For example, the superabsorbent material may be a polymeric material obtained by graft polymerisation of acrylic acid onto a chain of carboxymethyl cellulose. The superabsorbent material may comprise a chemically modified material selected from starch, cellulose and polymeric materials such as poly(vinyl alcohol) (PVA), poly(ethylene oxide) (PEO), and poly(acrylic acid). The poly(acrylic acid) may be a partially neutralised, lightly cross-linked poly(acrylic acid).

The terms "cross-linking" and "cross-linked" are used herein to refer to two or more polymer chains being linked by a primary bond, such as a covalent bond. The term "lightly cross-linked" is used herein to refer to embodiments wherein the number of cross-linking primary bonds in the superabsorbent material is less than the total number of possible cross-linking bonds.

In some embodiments, the superabsorbent material is selected from polymeric materials such as PVA, PEO, and poly(acrylic acid), preferably a partially neutralised, lightly cross-linked poly(acrylic acid). Typically, the superabsorbent material is a partially neutralised, lightly cross-linked poly(acrylic acid).

The superabsorbent material may be in the form of fibres. Typically, the superabsorbent material is in the form of non-woven fibres. The length of the fibres can be up to 100 mm, and is typically from 20-75 mm, more typically from 32 to 51 mm.

The delivery mechanism may be a wound dressing known in the art.

The composition of the present invention may be applied to the delivery mechanism by any suitable means known in the art.

The composition of the present invention may comprise a first component selected from the group consisting of chitosan, chitin, derivatives of chitosan, derivatives of chitin, and combinations thereof; at least one triprotic acid and at least one solubilising acid, wherein the first component is at least partially coated with the triprotic acid and the solubilising acid.

The composition may comprise a fibrous first component selected from the group consisting of chitosan, chitin, derivatives of chitosan, derivatives of chitin, and combinations thereof; at least one triprotic acid and at least one solubilising acid, wherein the fibres of the first component are at least partially coated with the triprotic acid and the solubilising acid.

Typically, the composition comprises a fibrous chitosan first component at least partially coated with a triprotic acid and a solubilising acid. Preferably, the composition comprises a nonwoven fibrous chitosan first component at least partially coated with citric acid and lactic acid. Preferably still, the composition comprises a nonwoven fibrous chitosan first component substantially fully coated with a mixture of citric acid and lactic acid According to a further aspect of the present invention, there is provided a wound dressing comprising a composition as described herein.

The wound dressing may be a wound dressing that gels upon contact with a fluid, such as wound exudate. In the field of gelling wound dressings, which focus on stemming blood flow from a bleeding wound, the composition of the present invention is particularly surprising since triprotic acids on nonwoven wound dressings tend not to gel and have been known to show detrimental effects on absorbency and water retention.

The wound dressing may comprise a composition as described herein and a delivery mechanism as described herein. The composition may be applied to the delivery mechanism by coating or the like. The composition and the delivery mechanism may form a layered wound dressing.

The composition of the present invention, or a wound dressing comprising such a composition, may also comprise additional components. Such additional components include, but are not limited to, antimicrobial agents; pharmaceutical agents; chelating agents; wetting agents such as surfactants; growth factors; cytokines; agents which absorb agents which delay healing such as MMP's (matrix metalloproteinases) and elastase; and/or another wound dressing component, such as calcium, vitamin K, fibrinogen, thrombin, factor VII, factor VIII, clays such as kaolin, oxidised regenerated cellulose, gelatin, or collagen, etc.

Suitable antimicrobial agents may be selected from the list comprising silver, polyhexamethylene biguanide (PHMB), iodine, octenidine, copper, chlorhexidine gluconate (CHG), miconazole, metronidazole and combinations of one or more thereof.

The antimicrobial agent may be coated onto or absorbed into the first component and/or a carrier material in the same manner as described herein in relation to the triprotic and/or solubilising acids.

The composition of the present invention may be mixed with other compositions useful in wound care. In some embodiments, the composition of the present invention may be mixed or blended with one or more haemostats. The haemostats may be in the form or fibres, granules, flakes, powder or any combination thereof. Preferably, the haemostat is in the form of granules.

For example, a composition of the present invention as described herein may be blended with a haemostat such as Celox® granules, a commercially available chitosan-based haemostat.

According to a further aspect of the present invention, there is provided a composition as described herein for use as a therapeutic agent.

According to a further aspect of the present invention, there is provided a composition as described herein for use in the treatment of wounds.

According to a further aspect of the present invention, there is provided a composition as described herein for use in disrupting and killing bacteria within a biofilm.

According to a further aspect of the present invention, there is provided a composition as described herein for use in preventing the formation of a biofilm.

According to a further aspect of the present invention, there is provided a method of manufacturing a composition comprising a first component selected from the group consisting of chitosan, chitin, derivatives of chitosan, derivatives of chitin, and combinations thereof; at least one triprotic acid and at least one solubilising acid, the method comprising the steps of:
(a) coating at least a portion of the first component with a mixture comprising the at least one triprotic acid and the at least one solubilising acid; and/or
(b) absorbing into at least a portion of the first component a mixture comprising the at least one triprotic acid and the at least one solubilising acid.

According to a further aspect of the present invention, there is provided a method of manufacturing a composition comprising a first component selected from the group consisting of chitosan, chitin, derivatives of chitosan, derivatives of chitin, and combinations thereof; at least one triprotic acid and at least one solubilising acid, the method comprising the steps of:
(a) mixing a triprotic acid with water and/or a solvent to provide a triprotic acid solution;
(b) mixing the triprotic acid solution with a solubilising acid solution prepared by mixing a solubilising acid with water and/or a solvent, to provide a mixed acid solution;
(c) optionally mixing the mixed acid solution with a solvent; and
(d) adding the first component to the solution obtained in step (c).

The method may further comprise the step (e) of drying the mixture obtained in step (d). The drying step may remove some or all of the solvent and/or water content of the composition.

For compositions wherein the first component comprises chitosan fibre, the solvent of steps (a) to (c) may typically be non-aqueous.

The further aspects of the present invention may incorporate any or all of the features described in respect of the first aspect of the present invention as desired or as appropriate.

Embodiments of the present invention will now be further described with reference to the following non-limiting examples and accompanying figure in which:

FIG. 1: is a graph showing the results from testing using the MBEC Assay for *Pseudomonas aeruginosa* ATCC 13359;

FIG. 2: is a graph showing the results from testing using the MBEC Assay for *Staphylococcus haemolyticus*;

FIG. 3: is a graph showing the results from testing using the MBEC Assay for MRSA 308;

FIG. 4: is a graph showing the results from testing using the CDC Reactor Model for *Pseudomonas aeruginosa* ATCC 10434;

FIG. 5: is a graph showing the results from testing using the CDC Reactor Model for *Staphylococcus haemolyticus* NCTC 11042;

FIG. 6: is a graph showing the results from testing using the CDC Reactor Model for Methicillin-resistant *Staphylococcus aureus* 308;

FIG. 7: is a graph showing the results from testing using the CDC Reactor Model for *Pseudomonas aeruginosa* ATCC 10434;

FIG. 8: is a graph showing the results from testing using the CDC Reactor Model for *Pseudomonas aeruginosa* ATCC 10434;

FIG. 9: is a graph showing the results from testing using the CDC Reactor Model for *Staphylococcus aureus*;

FIG. 10: is a graph showing the results from testing using the CDC Reactor Model for *Staphylococcus aureus*;

FIG. 11: is a graph showing the quantity of viable *Staphylococcus aureus* recovered from a pre-formed 24 hour biofilm after 24 hour treatment with each agent;

FIG. 12: is a graph showing the quantity of viable *Staphylococcus aureus* recovered from a pre-formed 72 hour biofilm after 24 hour treatment with each agent.

GENERAL METHODS OF SAMPLE PREPARATION

General Method 1: First Component and Triprotic Acid

Triprotic acid (e.g. citric acid) powder was dissolved in de-ionised water and then mixed with non-aqueous solvent (e.g. IPA). The first component, typically in nonwoven fibre form, was placed into the triprotic acid solution and allowed to absorb the solution. The solution was then dried using thermal drying, to leave a solid chitosan, chitin or derivative thereof coated with the triprotic acid.

General Method 2: First Component with Triprotic Acid and Monoprotic Acid

Triprotic acid (e.g. citric acid) powder was dissolved in de-ionised water and then mixed with a solubilising acid (e.g. lactic acid) solution. This was then mixed with non-aqueous solvent (e.g. IPA). The first component, typically in nonwoven fibre form, was placed into the mixed acid solution and allowed to absorb the solution. The solution was then dried using thermal drying, to leave a solid chitosan, chitin or derivative thereof coated with a mixture of triprotic acid and solubilising acid.

EXAMPLE COMPOSITIONS

The following are examples of compositions prepared according to the present invention.

Example 1 (Reference)

100% chitosan fibre nonwoven (1.35 g) was coated with citric acid (0.439 g) to provide a nominal 32.5% composition.

Example 2 (Reference)

100% chitosan fibre nonwoven (1.35 g) was coated with citric acid (0.027-0.068 g) to provide a nominal 2-5% composition.

Example 3 (Reference)

100% chitosan fibre nonwoven (1.35 g) was coated with citric acid (0.27-0.41 g) to provide a nominal 20-30% composition.

Example 4 (Reference)

100% chitosan fibre nonwoven (1.35 g) was coated with citric acid (0.81-0.94 g) to provide a nominal 60-70% composition.

Example 5

100% chitosan fibre nonwoven (1.35 g) was coated with citric acid (0.027-0.068 g) and lactic acid (0.34 g) to provide a nominal 2-5% triprotic acid and 25% monoprotic acid composition.

Example 6

100% chitosan fibre nonwoven (1.35 g) was coated with citric acid (0.27-0.41 g) and lactic acid (0.34 g) to provide a nominal 20-30% triprotic acid and 25% monoprotic acid composition.

Example 7

100% chitosan fibre woven (1.35 g) was coated with citric acid (0.81-0.94 g) and lactic acid (0.41 g) to provide a nominal 60-70% triprotic acid and 30% monoprotic acid composition.

Example 8

100% chitosan fibre nonwoven (1.35 g) was coated with citric acid (0.04 g) and lactic acid (0.2 g) to provide a nominal 3% triprotic acid and 15% monoprotic acid composition.

Example 9

100% chitosan fibre nonwoven (1.35 g) was coated with citric acid (0.34 g) and lactic acid (0.2 g) to provide a nominal 25% triprotic acid and 15% monoprotic acid composition.

Example 10

100% chitosan fibre nonwoven (1.35 g) was coated with citric acid (0.81 g) and lactic acid (0.27 g) to provide a nominal 60% triprotic acid and 20% monoprotic acid composition.

Example 11

100% chitosan fibre nonwoven (1.35 g) was coated with citric acid (0.41 g) and lactic acid (0.34 g) to provide a nominal 30% triprotic acid and 25% monoprotic acid composition.

Example 12

100% chitosan fibre nonwoven (1.35 g) was coated with citric acid (0.54 g) and lactic acid (0.34 g) to provide a nominal 40% triprotic acid and 25% monoprotic acid composition.

Example 13

100% chitosan fibre nonwoven (1.35 g) was coated with citric acid (0.54 g) and lactic acid (0.41 g) to provide a nominal 40% triprotic acid and 30% monoprotic acid composition.

EXAMPLE WOUND DRESSINGS

Example 14 (Reference)

A composition of the present invention is prepared containing nominally 2 g 100% chitosan fibre nonwoven in 8 g de-ionised water with 0.6 g citric acid. The composition was coated onto the surface of a non-reticulated polyurethane foam and allowed to dry. The foam containing the dried composition of the present invention was then adhesive bonded to a polyurethane foam, distal to a bonded polyurethane film layer, to form a wound contact layer.

Example 15 (Reference)

A composition of the present invention is prepared containing nominally 2 g 100% chitosan fibre nonwoven in 8 g de-ionised water with 0.6 g citric acid. The composition was coated onto the surface of a woven viscose textile and allowed to dry.

MBEC Assay 1

To determine the efficacy of antimicrobials against biofilms of various microorganisms, an MBEC (Minimum Biofilm Eradication Concentration) Assay was used.

The MBEC Assay is a high throughput screening assay used to determine the efficacy of antimicrobials against biofilms of various microorganisms. The MBEC Biofilm Inoculator consists of a plastic lid with 96 pegs and a corresponding base. There are two types of bases that may be used with the MBEC lid. One base contains 96 individual wells. The individual wells allow for the growth of a variety of microorganisms on the same peg lid. The other type of base is a corrugated through base that can contain only a single microorganism. Biofilms are established on the pegs under batch conditions (no flow of nutrients into or out of an individual well) with gentle mixing. The established biofilm is transferred to a new 96 well plate for antimicrobial efficacy testing. The assay design allows for the simultaneous testing of multiple biocides at multiple concentrations with replicate samples, making it an efficient screening tool.

Test Microorganisms
*Pseudomonas aeruginosa* ATCC 13359
*Staphylococcus haemolyticus*
MRSA 308

Comparative Samples Tested

Control: Phosphate buffered saline (PBS)

Sample A: 100% chitosan fibre nonwoven with Ag (nominally 1%) and lactic acid to provide a nominal 25% monoprotic acid composition Sample B: Carboxymethylated cellulose fibre nonwoven with Ag (nominally 1%) (Aquacel Ag®)

Sample C: 100% Chitosan fibre nonwoven with lactic acid to provide a nominal 25% monoprotic acid composition Sample D: 100% Chitosan fibre nonwoven with acetic acid to provide a nominal 25% monoprotic acid composition Sample E: 100% Chitosan fibre nonwoven with citric acid to provide a nominal 25% triprotic acid composition Preparation of Bacterial Inoculum A 24 hour culture of each microorganism was harvested from either a Tryptone Soya Agar (TSA) plate or Brain Heart Infusion Agar (BHIA) plate and suspended in either 20 ml of Tryptone Soya Broth (TSB) or 20 ml of Brain Heart Infusion Broth (BHIB). The resultant bacterial suspension was diluted to give an initial OD590=0.10±0.03, which corresponds to a bacterial concentration of $10^8$ cfuml$^{-1}$. This initial inoculum was serially diluted a further six times in order to represent progressively lower bacterial loads (i.e. $10^7$, $10^6$, $10^5$, $10^4$, $10^3$ cfuml$^{-1}$). The starting bacterial concentration for each organism was typically $1\times10^8 \pm 5\times10^7$ cfuml$^{-1}$.

MBEC Assay

The biofilms of each microorganism were grown on pin lid projections of a microtitre plate for 48 hours at 37° C., 50 rpm. After 48 hours the pin lids were removed, washed briefly in Phosphate Buffered Saline (PBS) to remove planktonic bacteria and then placed in the agent challenge plate for 24 hours. For the preparation of challenge plate for the wound dressings, 1 cm² pieces were cut using sterile scissors and placed into the designated wells of a microtitre plate. The challenge plate for the granule test agents was prepared by weighing out 30 mg±3 mg of each granule formulation into the wells of a microtitre plate. The wound dressings and the granules were then activated with 150 µl of PBS. Following treatment, the pin lid projections were washed twice in PBS, then transferred into 200 µl of neutraliser and placed in a sonic water-bath for 5 minutes in order to recover remaining attached bacteria. Serial dilutions were carried out on the resultant recovery broth and drop plates were used to quantify the recovered bacteria. All samples were tested in triplicate unless otherwise stated.

The results are shown in Table 1 and FIGS. 1 to 3. The results in FIGS. 1 to 3 relate to Samples B, C and E.

It is clear from the graphs shown in FIGS. 1 to 3 that Sample E comprising chitosan coated with a triprotic acid is effective against all three microorganisms tested. Sample C comprising chitosan fibres coated with a monoprotic acid showed microorganism concentrations for all three microorganisms tested. Finally, Sample B comprising carboxymethylated cellulose with silver showed good results for *Staphylococcus haemolyticus* but was not effective against either *Pseudomonas aeruginosa* ATCC 13359 and MRSA 308.

Sample I: 100% Chitosan fibre nonwoven with 3% citric acid. This equates to 1.35 g chitosan and 0.04 g citric acid (reference Example 2).

Sample J: 100% Chitosan fibre nonwoven with 25% citric acid. This equates to 1.35 g chitosan and 0.34 g citric acid (reference Example 3).

Sample K: 100% Chitosan fibre nonwoven with 60% citric acid. This equates to 1.35 g chitosan and 0.81 g citric acid (reference Example 4).

The samples were prepared following the methods described hereinbefore.

Dressing samples were cut into approximately 1.5 cm² pieces before use. Phosphate Buffered Saline (PBS) was used as the control.

Preparation of Bacterial Inoculum

A 24 hour culture of the test bacteria was harvested from a Tryptone Soya Agar (TSA) plate using a sterile swab and re-suspended in 20 ml of Tryptone Soya Broth (TSB). The bacterial suspension was diluted to give an $OD590=0.10\pm0.03$ which corresponds to a bacterial concentration of $108\pm5\times10^7$ cfuml$^{-1}$. This was further diluted in TSB and used as the inoculum for the CDC reactor containing the test coupons. The CDC reactor was incubated for 48 hours at 37° C., shaking at 50 rpm in order to encourage biofilm growth.

TABLE 1

Test results following MBEC Assay

| | Organisms | | | | | |
|---|---|---|---|---|---|---|
| Sample | P. aeruginosa (1 strain) | P. aeruginosa (2 strain) | E. faecillis (VRE) | MRSA | S. epidermidis | S. haemolyticus |
| A | Comparable to untreated control | Comparable to untreated control | >Log 4 | Ranged between Log2 and >log 4 | >Log 4 | >Log 4 |
| B | ≤Log 3 | Comparable to untreated control | Comparable to untreated control | Ranged between Log2 and >log 4 | Log 2 | >Log 4 |
| C | Comparable to untreated control | ≤Log 2 | >Log 4 | Ranged between Log2 and >log 4 | >Log 4 | >Log 4 |
| D | >Log 4 | ≤Log 3 | >Log 4 | Ranged between Log2 and >log 4 | >Log 4 | ≤Log 2 |
| E | >Log 4 | >Log 4 | >Log 4 | >Log 4 | >Log 4 | >Log 4 |

CDC Reactor Model 1

To determine the biofilm removal capabilities of seven wound dressings, against three bacterial species, using a CDC reactor method.

Test Microorganisms

*Staphylococcus haemolyticus* NCTC 11042

*Pseudomonas aeruginosa* ATCC 10434

Methicillin-resistant *Staphylococcus aureus* 308

Samples Tested

Control: Phosphate buffered saline (PBS)

Sample F: 100% Chitosan fibre nonwoven with 15% lactic acid and 3% citric acid. This equates to 1.35 g chitosan, 0.2 g lactic acid and 0.04 g citric acid (Example 8).

Sample G: 100% Chitosan fibre nonwoven with 15% lactic acid and 25% citric acid. This equates to 1.35 g chitosan, 0.2 g lactic acid and 0.34 g citric acid (Example 9).

Sample H: 100% Chitosan fibre nonwoven with 20% lactic acid and 60% citric acid. This equates to 1.35 g chitosan, 0.27 g lactic acid and 0.81 g citric acid (Example 10).

Biofilm Treatment

After 48 hours the test coupons were removed from the CDC reactor and washed 3 times in sterile PBS in order to remove planktonic bacteria. The washed coupons were then treated by sandwiching the coupon between two 1.5 cm² dressing samples. The dressings were activated prior to testing by the addition of 350 µl PBS (75% saturation) to each 1.5 cm² piece. Control coupons were submerged in 2 µl of PBS for *P. aeruginosa* (or in the case of *S. haemolyticus* and MRSA in 2 ml PBS+0.1% TSB). All samples were tested in triplicate. Microorganisms were recovered from the coupons after 24 hours treatment and quantified by performing serial dilutions and drop plates.

The results are shown in FIGS. 4 to 6.

It is clear from the graphs shown in FIGS. 4 to 6 that Samples G, H and K are effective against all three microorganisms tested. Samples G and H comprise chitosan fibres coated with a triprotic acid and a monoprotic acid. Sample K comprises a chitosan fibre coated with a higher amount of a triprotic acid. Whilst Samples F, I and J were effective against methicillin-resistant *Staphylococcus aureus* 308, they were less effective against both *Staphylococcus haemolyticus* NCTC 11042 and *Pseudomonas aeruginosa* ATCC 10434.

The results of the CDC Reactor Model show that a chitosan coated with increasing amounts of triprotic acid, e.g. around 60%, is more effective against microorganisms than a lower amount of around 25% or less. Also, the results show that including a monoprotic acid with a triprotic acid can be effective in reducing the amount of triprotic acid required, e.g. reducing the amount of triprotic acid to around 25%.

CDC Reactor Model 2

To determine the biofilm removal capabilities of six wound dressings, against two bacterial species, using the CDC reactor method.

Test Microorganisms

*Staphylococcus haemolyticus* NCTC 8325
*Pseudomonas aeruginosa* ATCC 10434

Samples Tested

Control: Phosphate buffered saline (PBS)

Sample L: 100% Chitosan fibre nonwoven with 25% lactic acid and 30% citric acid. This equates to 1.35 g chitosan, 0.34 g lactic acid and 0.41 g citric acid (Example 11).

Sample M: 100% Chitosan fibre nonwoven with 25% lactic acid and 40% citric acid. This equates to 1.35 g chitosan, 0.34 g lactic acid and 0.54 g citric acid (Example 12).

Sample N: 100% Chitosan fibre nonwoven with 30% lactic acid and 40% citric acid. This equates to 1.35 g chitosan, 0.41 g lactic acid and 0.54 g citric acid (Example 13).

Sample O: 100% Chitosan fibre nonwoven.

Sample P: 55% Chitosan fibre/45% Viscose fibre nonwoven with 25% lactic acid. This equates to 0.74 g chitosan fibre, 0.61 g Viscose fibre and 0.34 g lactic Acid Sample Q: Carboxymethylcellulose nonwoven with ionic silver-containing, antibiofilm formulation.

The samples were prepared following the methods described hereinbefore.

Dressing samples were cut into approximately 1.5 cm² pieces before use. Phosphate Buffered Saline (PBS) was used as the control.

Preparation of Bacterial Inoculum

A 24 hour culture of each microorganism was harvested from a Tryptone Soya Agar (TSA) plate and resuspended in 20 ml of Tryptone Soya Broth (TSB). The resultant bacterial suspension was diluted to give an initial $OD_{590}=0.10\pm0.03$, which corresponds to a bacterial concentration of $10_8\pm5\times10_7$ cfuml$_{-1}$. This was further diluted to approximately $10_7$ cfuml$_{-1}$ in TSB and was used as the initial inoculum for the CDC reactor. The CDC reactor was incubated for 24 and 72 hours at 37° C., shaking at 50 rpm in order to encourage biofilm growth.

Biofilm Treatment

After 24 hours and 72 hours the test coupons were removed from the CDC reactor and washed 3 times in sterile Phosphate Buffered Saline (PBS) in order to remove planktonic bacteria. The washed coupons were then treated by sandwiching each coupon between two pieces of wound dressing material. The dressings were activated prior to testing by the addition of 350 µl PBS containing 1% TSB. Control coupons were submerged in 2 ml of PBS containing 1% TSB. Following the 24 hour treatment period the coupons were placed in 2 ml of neutraliser and sonicated for 15 minutes to recover remaining attached bacteria. Serial dilutions were carried out on the resultant recovery broth and drop plates were used to quantify the recovered bacteria. All samples were tested in triplicate.

The results are shown in FIGS. 7 to 10.

It is clear from the graphs shown in FIGS. 7 to 10 that Samples L, M and N of the present invention are effective against both microorganisms tested. Whilst Samples Q and P were effective against *Staphylococcus aureus*, they were less effective against *Pseudomonas aeruginosa* ATCC 10434.

MBEC Assay 2

Test Microorganism

*Staphylococcus aureus* NCTC 8325

Agents Tested

| Control | Phosphate Buffered Saline (PBS) + 1% Tryptone Soya Broth |
| --- | --- |
| 1 | 2.5% Chitosan with 50% citric acid and 25% lactic acid |
| 2 | Chitosan with 30% citric acid and 25% lactic acid |
| 3 | Chitosan with 50% citric acid and 25% lactic acid |
| 4 | Chitosan with 15% citric acid and 25% lactic acid |
| 5 | Chitosan with 50% citric acid (reference) |

All test agents were prepared by coating chitosan granules having a degree of deacetylation >75% with the specified acid(s) using a non-aqueous solvent. This formed a solid chitosan salt in the form of a granule. The granules were then mixed into a gel formulation using de-ionised water with the gel containing between 5-10% chitosan salt.

MBEC Assay

The *S. aureus* biofilm was grown on pin lid projections of a microtitre plate for 24 hours and 72 hours at 37° C. After 24 hours and 72 hours the pin lids were removed, washed briefly in sterile Phosphate Buffered Saline (PBS) to remove planktonic bacteria and then placed in the agent challenge plate for 24 hours. For the preparation of the challenge plate an amount of each gel formulation was placed into the wells of a microtitre plate. Positive and negative control pin lid projections were placed in PBS+1% TSB. Following treatment, the pin lid projections were washed twice in PBS and then placed in a neutraliser. Plates were sonicated. Serial dilutions were carried out on the resultant recovery broth and drop plates were used to quantify the recovered bacteria. All samples were tested in triplicate.

Twenty-Four Hour Biofilm

Figure 1:
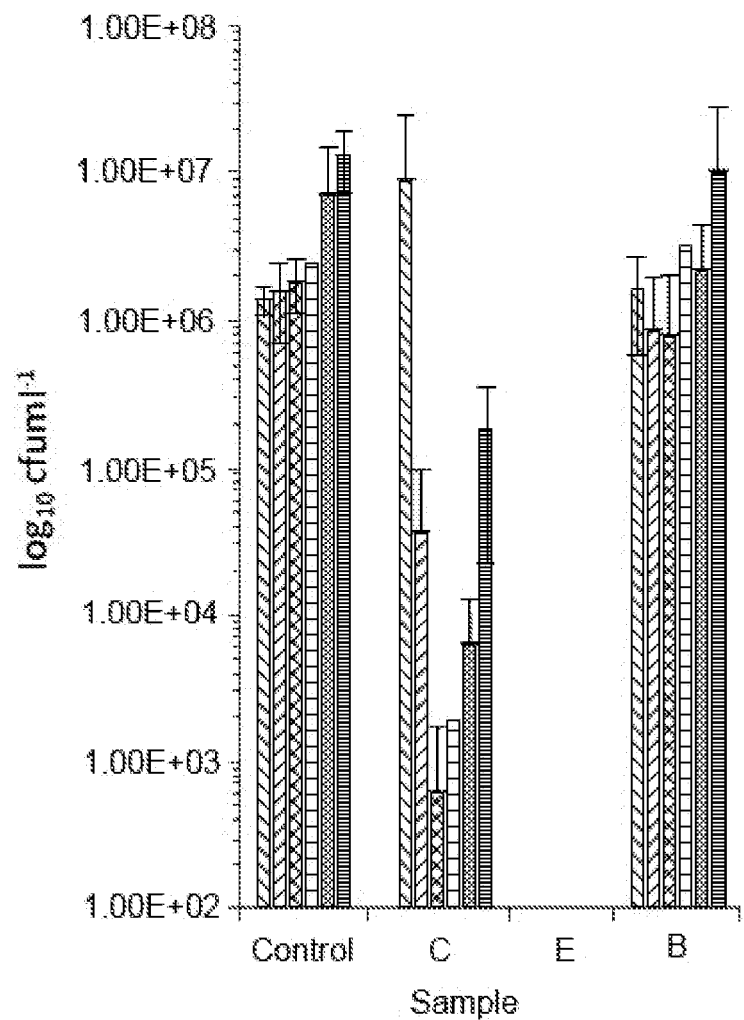
Figure 2:
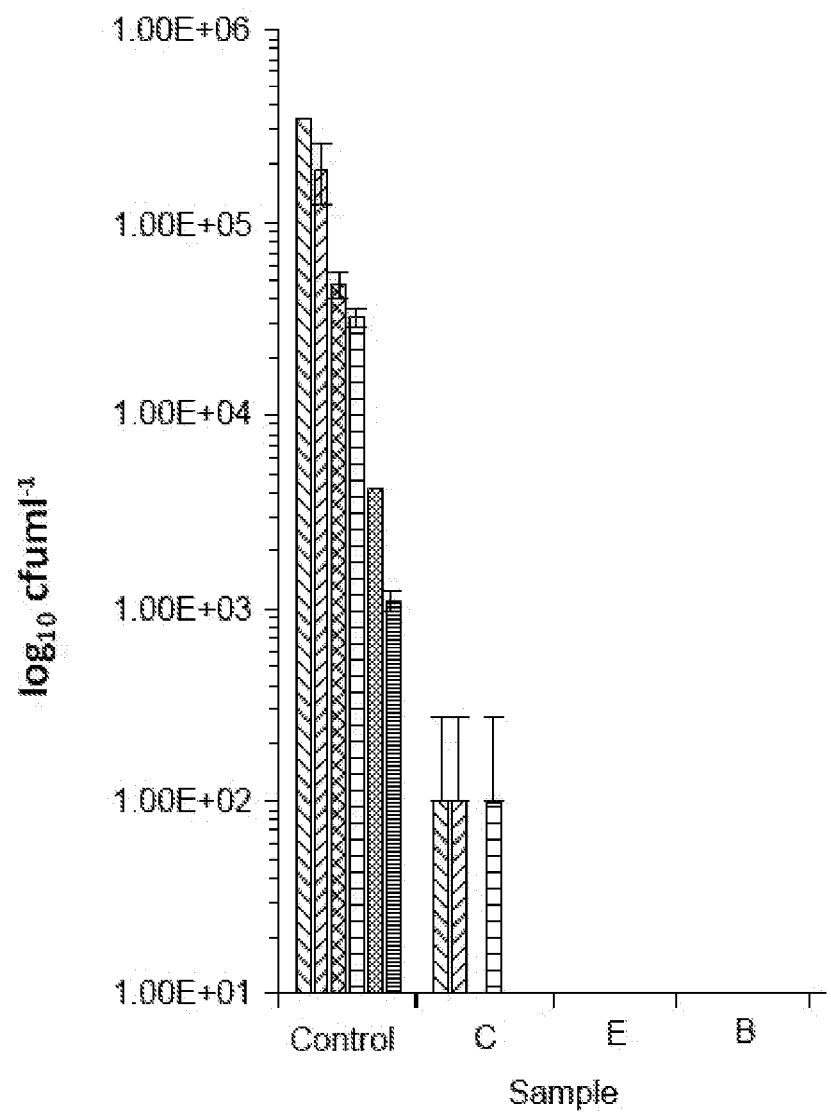
Figure 3:
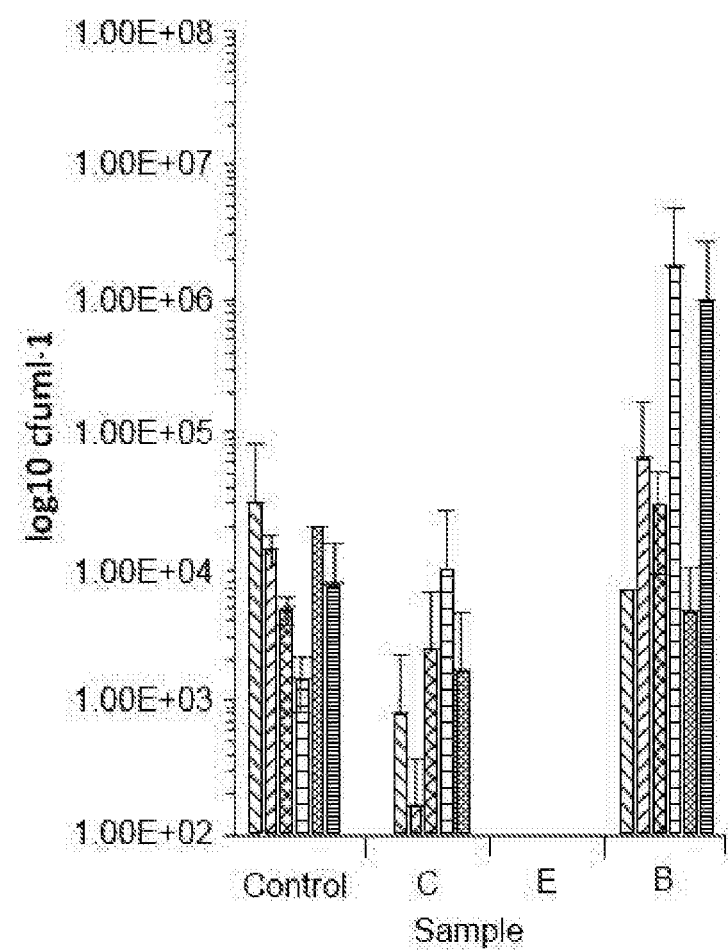
Figure 4:
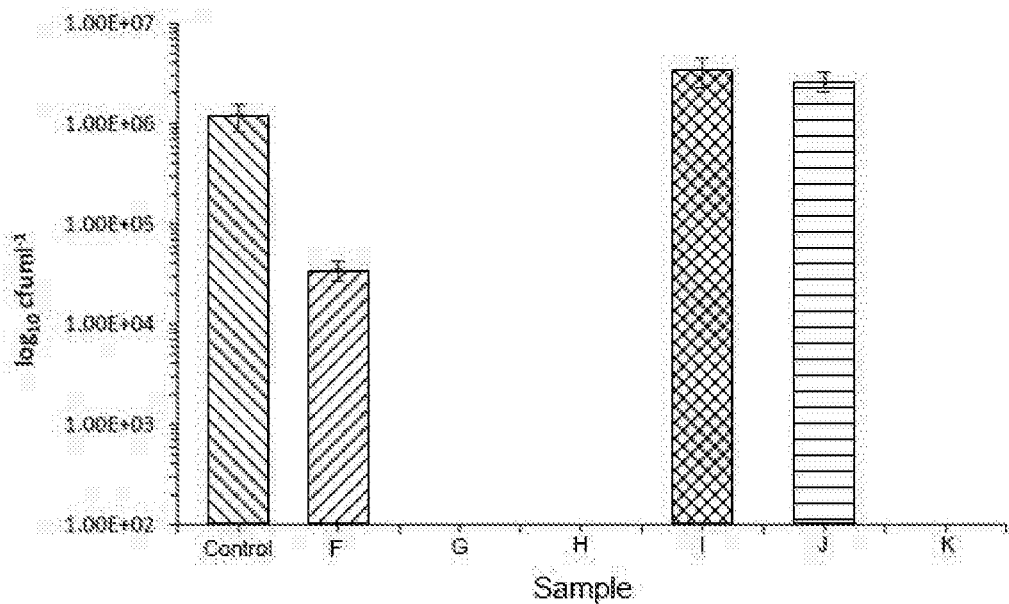
Figure 5:
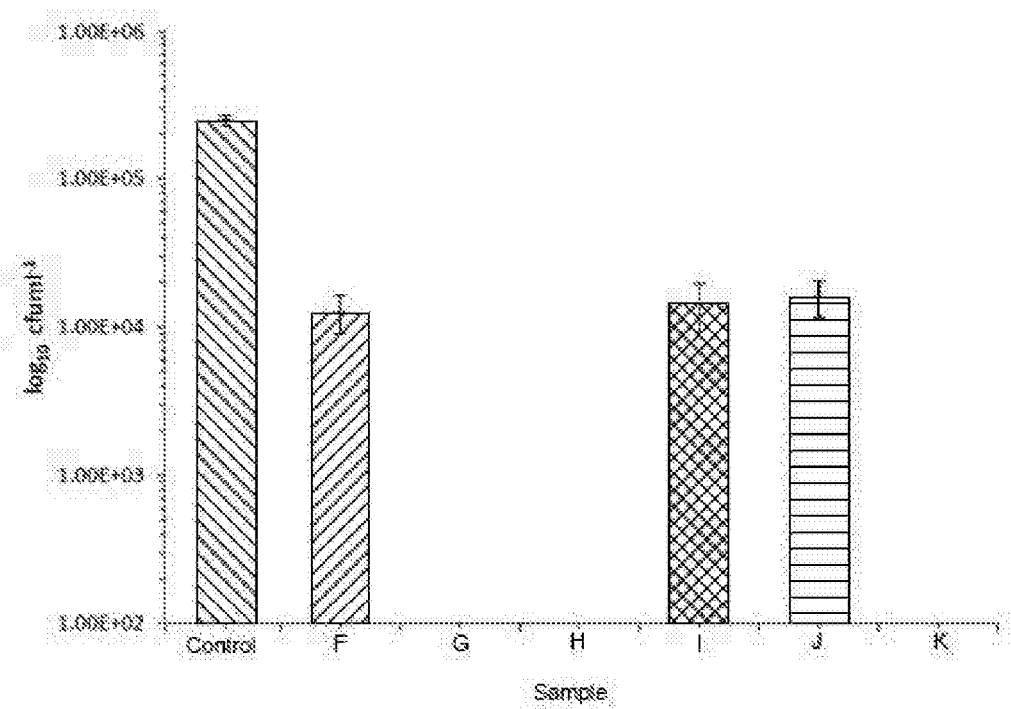
Figure 6:
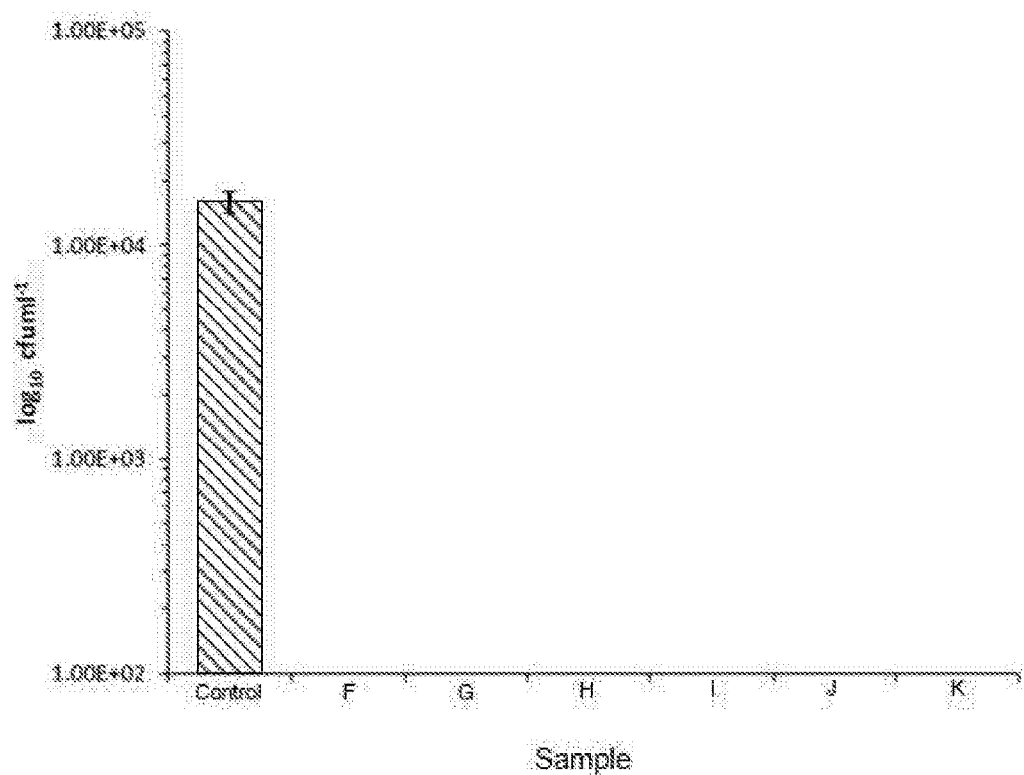
Figure 7:
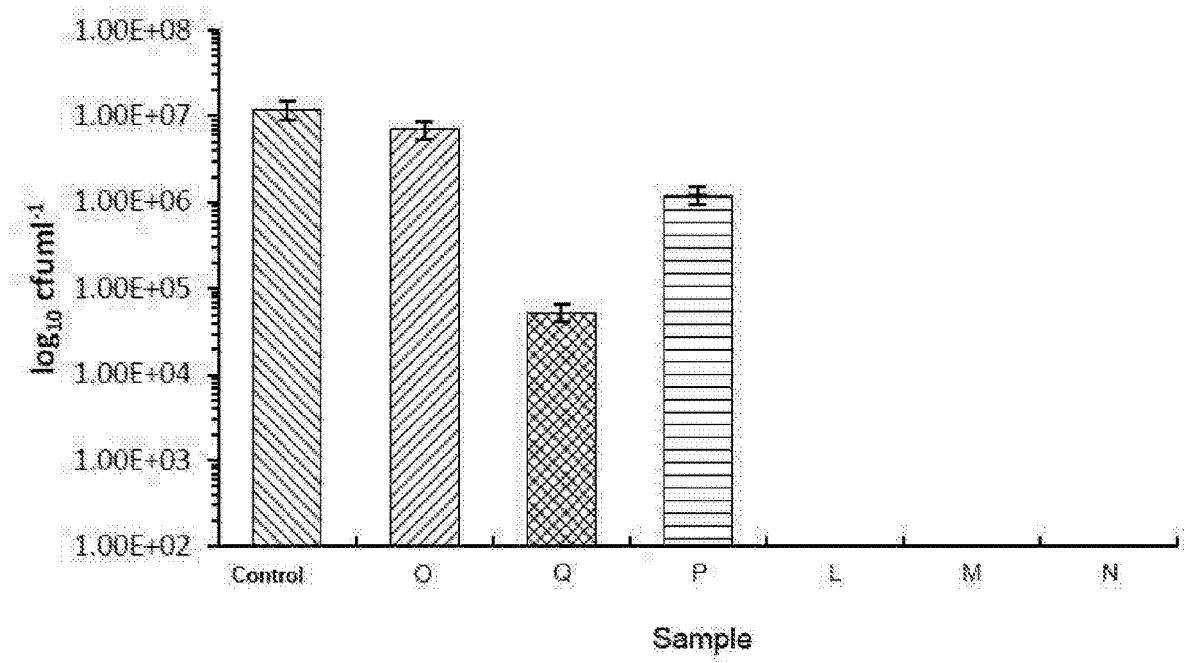
FIG. 7 shows the quantity of viable *Pseudomonas aeruginosa* recovered from 24 hour pre-formed biofilms following 24 hours treatment with the sample wound dressings. Controls were treated with PBS+1% TSB.
Figure 8:
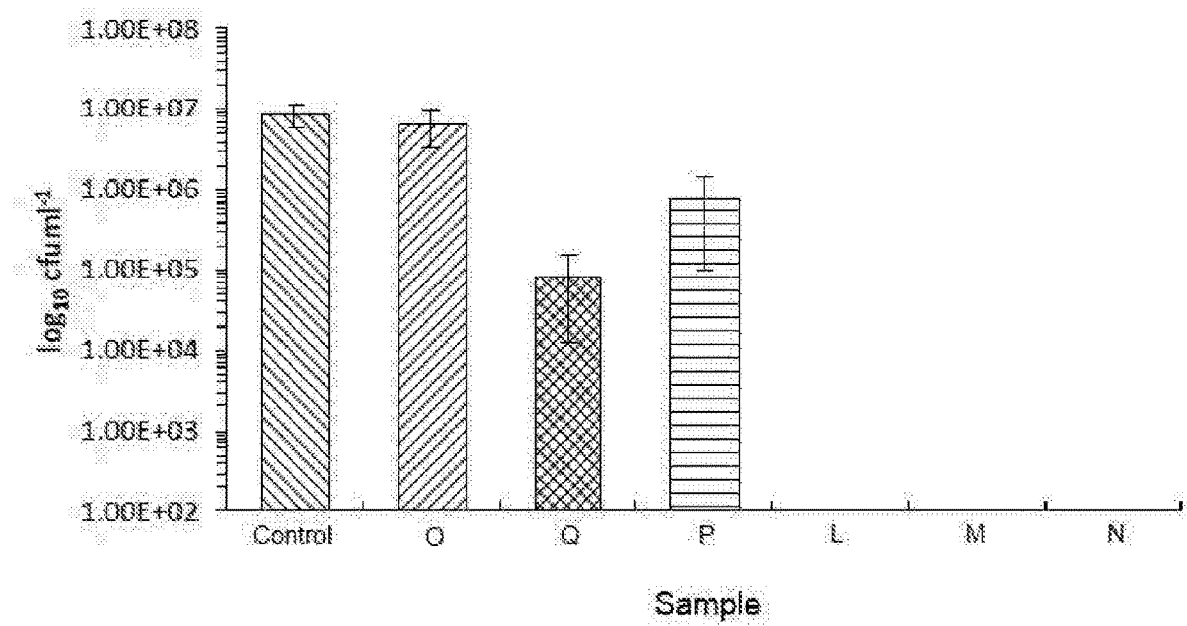
FIG. 8 shows the quantity of viable *Pseudomonas aeruginosa* recovered from 72 hour pre-formed biofilms following 24 hours treatment with the sample wound dressings. Controls were treated with PBS+1% TSB.
Figure 9:
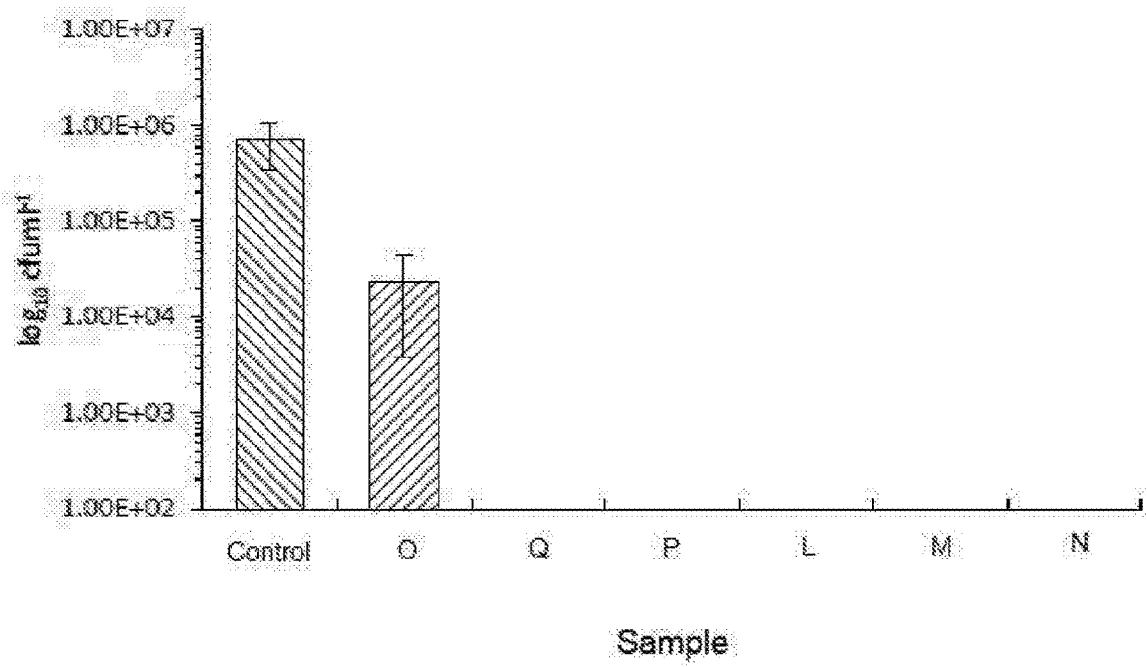
FIG. 9 shows the quantity of viable *Staphylococcus aureus* recovered from 24 hour pre-formed biofilms following 24 hours treatment with the sample wound dressings. Controls were treated with PBS+1% TSB.
Figure 10:
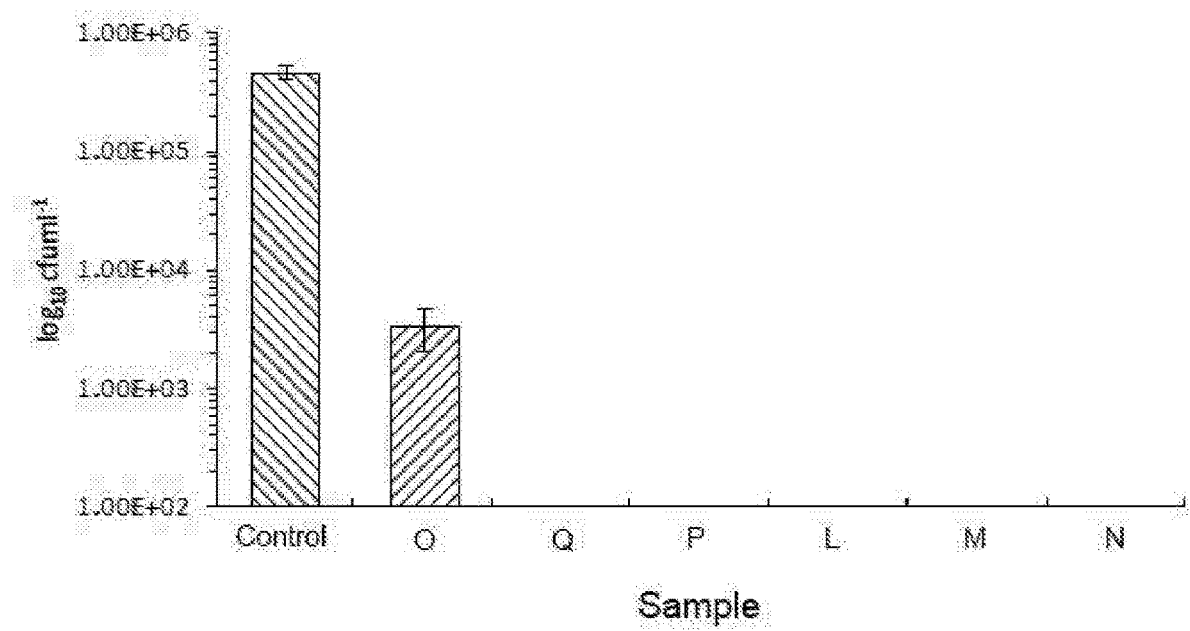
FIG. 10 shows the quantity of viable *Staphylococcus aureus* recovered from 72 hour pre-formed biofilms following 24 hours treatment with the sample wound dressings. Controls were treated with PBS+1% TSB.
Figure 11:
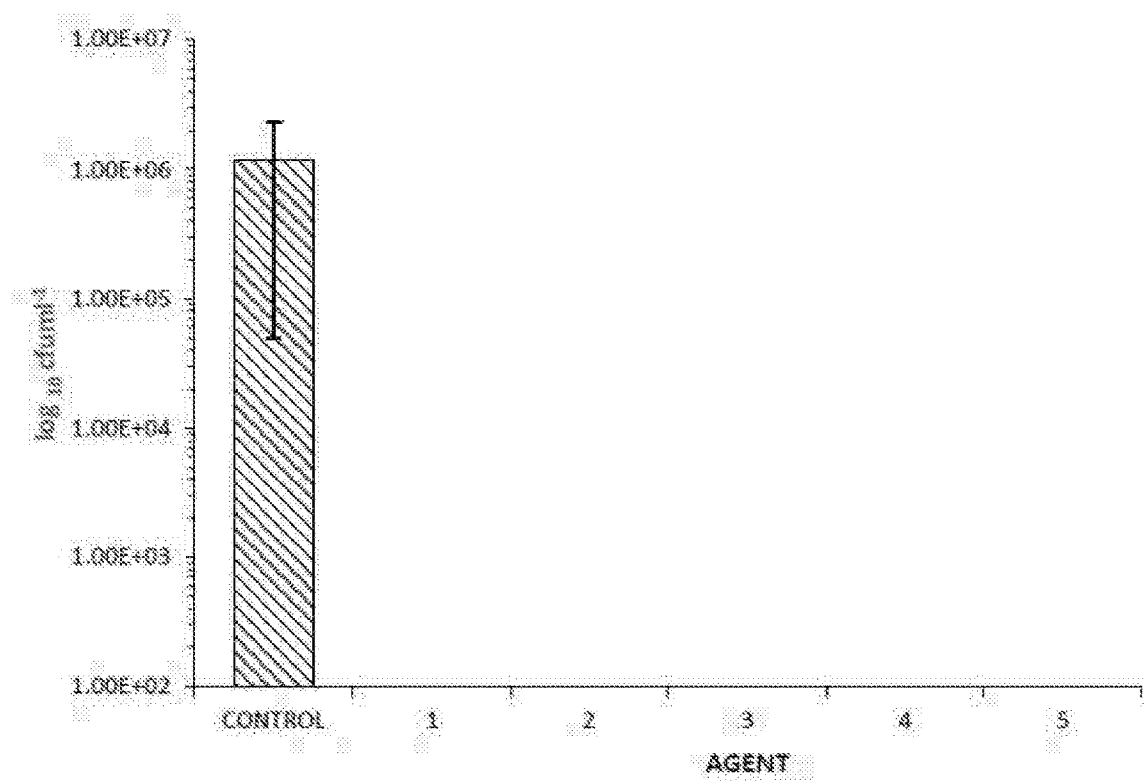

All the agents tested successfully reduced the number of viable bacteria recovered from within the pre-formed 24 hour biofilms of *S. aureus* after treatment for 24 hours at 37° C., as shown in FIG. 11. This represented a 5.84±0.53 log reduction in viable bacteria compared with the untreated controls.

Seventy-Two Hour Biofilm

Figure 12:
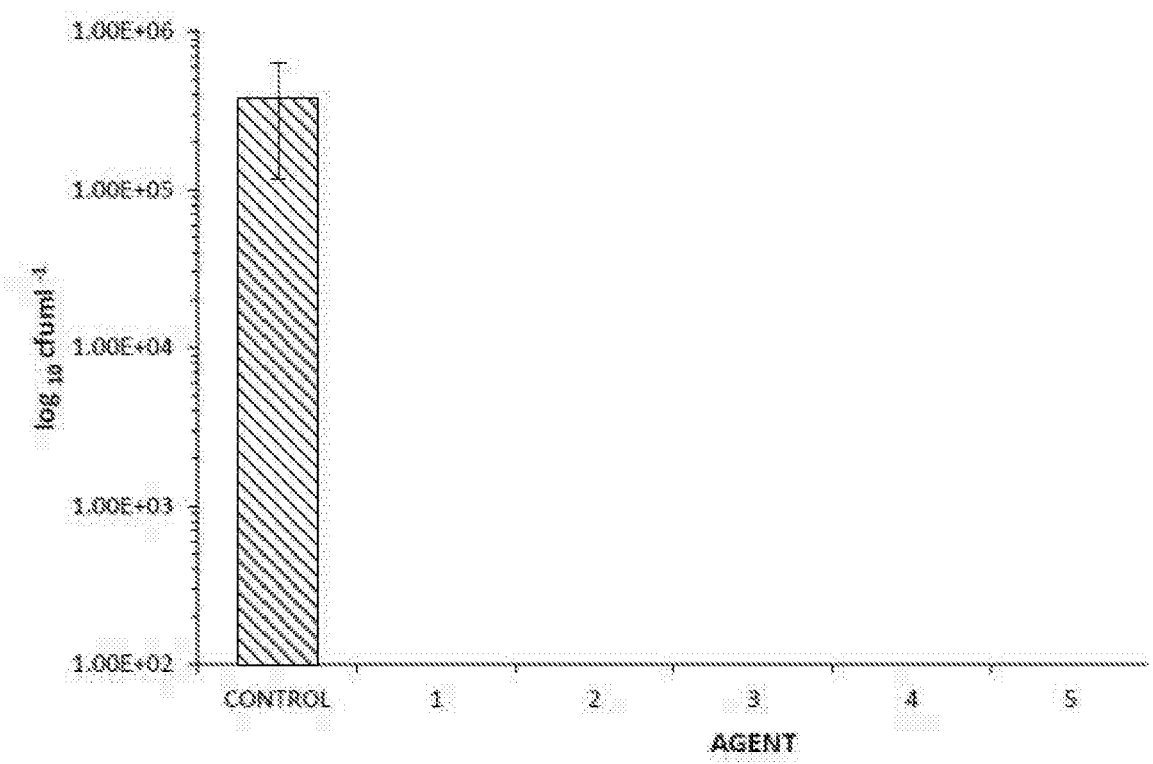

All the agents tested successfully reduced the number of viable bacteria recovered from within the pre-formed 72 hour biofilms of *S. aureus* after treatment for 24 hours at 37° C., as shown in FIG. 12. For each agent this represented a 5.52±0.22 log reduction in viable bacteria compared with the untreated controls.

It is of course to be understood that the present invention is not intended to be restricted to the foregoing examples which are described by way of example only.

The invention claimed is:

1. A composition comprising a fibrous first component selected from the group consisting of chitosan, chitin, derivatives of chitosan, derivatives of chitin, and any combination thereof; at least one triprotic acid and at least one solubilizing acid, wherein the triprotic acid is present in an amount of at least 25% of the first component.

2. The composition as claimed in claim 1, wherein the first component is non-antimicrobial.

3. The composition as claimed in claim 1, wherein the ratio of the first component to the at least one triprotic acid is at least 2:1; and/or wherein the ratio of the at least one triprotic acid to the at least one solubilising acid is at least 1:1.

4. The composition as claimed in claim 1, wherein the first component is chitosan; and/or wherein the triprotic acid is citric acid.

5. The composition as claimed in claim 1, wherein the first component has a degree of de-acetylation greater than 70%; and/or wherein the first component has a viscosity greater than 150 cps in 1% acetic acid solution.

6. The composition as claimed in claim 1, wherein the fibrous first component are nonwoven.

7. The composition as claimed in claim 1, wherein the triprotic acid is present in an amount of around 25 to 60% of the first component.

8. The composition as claimed in claim 1, wherein the composition is in the form of granules, flakes, powder, nonwoven textile or knitted textile.

9. The composition as claimed in claim 1, wherein the solubilising acid is a monoprotic acid.

10. The composition as claimed in claim 9, wherein the monoprotic acid is selected from the group consisting of lactic acid, formic acid, acetic acid, hydrochloric acid, and mixtures thereof.

11. The composition as claimed in claim 1, wherein the triprotic acid and the solubilising acid are coated onto the first component.

12. The composition as claimed in claim 1, wherein the solubilising acid is present in an amount of from 2-50% of the first component, and optionally wherein the solubilising acid is present in an amount of from 15-30% of the first component.

13. The composition as claimed in claim 1, wherein the triprotic acid and/or the solubilising acid is coated onto a carrier material.

14. The composition as claimed in claim 1, further comprising an additional component selected from the group consisting of antimicrobial agents; pharmaceutical agents; chelating agents; wetting agents; growth factors; cytokines; agents which absorb agents which delay healing; calcium; vitamin K; fibrinogen; thrombin; factor VII; factor VIII; clays; oxidised regenerated cellulose; gelatin; and collagen.

* * * * *